(12) United States Patent
Leiboff

(10) Patent No.: US 6,716,209 B2
(45) Date of Patent: Apr. 6, 2004

(54) LOOP OSTOMY DEVICE AND METHODS FOR ITS USE

(76) Inventor: Arnold Robert Leiboff, 5 Perigee Dr., Stony Brook, NY (US) 11790

( * ) Notice: Subject to any disclaimer, the term of this patent is extended or adjusted under 35 U.S.C. 154(b) by 0 days.

(21) Appl. No.: 10/082,524

(22) Filed: Feb. 22, 2002

(65) Prior Publication Data

US 2003/0163121 A1 Aug. 28, 2003

(51) Int. Cl.⁷ .............................. A61B 17/00
(52) U.S. Cl. .......................... 606/1; 604/327
(58) Field of Search ................. 128/897, 898, 128/899; 604/327, 328, 332, 336, 337, 338, 339, 340, 341, 342, 343, 344; 606/139, 1

(56) References Cited

U.S. PATENT DOCUMENTS

| | | | |
|---|---|---|---|
| 3,779,247 A | | 12/1973 | Nolan et al. |
| 4,067,339 A | | 1/1978 | Chiulli |
| 4,465,486 A | | 8/1984 | Hill |
| 4,671,272 A | * | 6/1987 | Steer ................... 128/303 R |
| 4,828,553 A | * | 5/1989 | Nielsen ................... 604/339 |
| 5,026,361 A | | 6/1991 | Matysiak |
| 5,456,246 A | | 10/1995 | Schmieding et al. |
| 5,549,619 A | | 8/1996 | Peters et al. |
| 5,758,663 A | * | 6/1998 | Wilk et al. ................. 128/898 |
| 5,810,854 A | | 9/1998 | Beach |
| 5,919,233 A | * | 7/1999 | Knopf et al. ................ 623/11 |
| 5,941,860 A | * | 8/1999 | Wheeler ................. 604/327 |

OTHER PUBLICATIONS

Article–Securing the Loop–Historic Review of the Methods Used for Creating a Loop Colostomy (John M. Corman, BA. and Dan B. Odenheimer, M.D.)–Read in Part at the Meeting of the American Society of Colon and Rectal Surgeons. (Nov. 1991).

* cited by examiner

Primary Examiner—Roy D. Gibson
Assistant Examiner—Aaron Roane
(74) Attorney, Agent, or Firm—Galgano & Burke

(57) ABSTRACT

A loop ostomy device includes a flexible rod having coupling members at its ends. The rod is rigid enough to support a bowel loop but flexible enough to bend into a loop and couple its ends together. Methods for using the appliance are also disclosed.

15 Claims, 6 Drawing Sheets

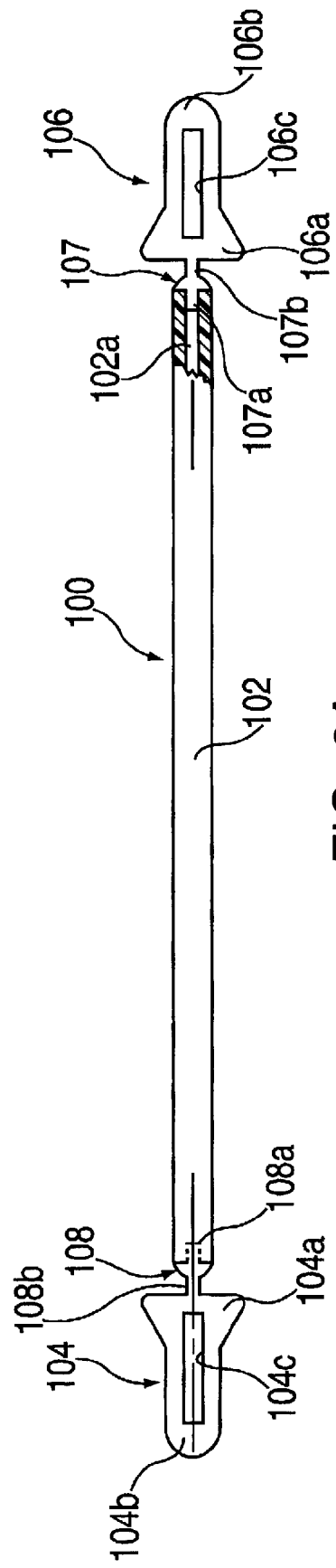
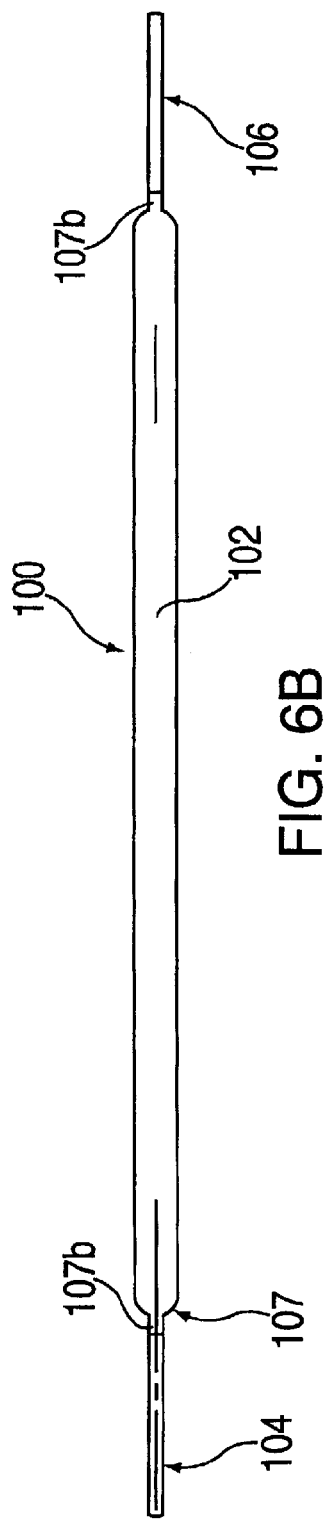
FIG. 6A
FIG. 6B

LOOP OSTOMY DEVICE AND METHODS FOR ITS USE

BACKGROUND OF THE INVENTION

1. Field of the Invention

The invention relates generally to abdominal surgery. More particularly, the invention relates to a loop ostomy device used to maintain a portion of the bowel outside of the body and to methods for using such a device.

2. State of the Art

Some abdominal surgery operations require a loop of the bowel to be maintained temporarily or permanently outside the body. These procedures are generally referred to as a "loop ostomy", "loop colostomy" or a "loop ileostomy" because a loop of bowel is pulled through an incision. In such a procedure, a pouch or similar container is fixed to the skin over the bowel via an adhesive backed wafer. The pouch and wafer which are either made as a one-piece integral unit or as a two piece assembly comprised of a wafer with a flange and a pouch with a flanged open end are commonly referred to as an ostomy appliance.

There are several known apparatuses and kits used when performing a loop ostomy procedure. One such kit is distributed under the trademark GENTLE TOUCH® by ConvaTec, Skillman, N.J. The kits generally include an adhesive-backed wafer having a coupling flange, a drainable pouch adapted to be removably coupled to the coupling flange, and a rod which is used to prevent the loop of bowel from retreating into the body. The kits are available in different sizes based on the diameter of the coupling flange. Prior art FIGS. 1–5 illustrate a portion of the loop ostomy procedure utilizing the GENTLE TOUCH® kit from ConvaTec.

Referring now to prior art FIG. 1, the GENTLE TOUCH® kit includes a loop ostomy device in the form of a rod 10 which is substantially the same as the device described in U.S. Pat. No. 4,671,272. The rigid rod has a fixed cross-piece 12 at one end and a rotatable cross-piece 14 at the other end. Before installing the rod, the rotatable cross-piece 14 is rotated to the position shown in FIG. 1.

After the abdomen is incised and a loop of bowel is exteriorized, the rod 10 is inserted through the mesentery 15 of the bowel 16 as shown in prior art FIG. 2. The rotatable cross-piece 14 is then rotated to the position shown in prior art FIG. 3 so as to prevent the rod from sliding free under the highly slippery surface of the bowel 16.

With the rod in position, a hole 18 is cut in the wafer 20 as shown in prior art FIG. 4. The adhesive backing is removed from the wafer 20; it is positioned over the stoma; and the rod 10 is carefully manipulated so that it lies on top of the wafer 20 within the flange 22 as shown in prior art FIG. 5. Other (not illustrated) steps in the procedure include incising the bowel 16 and coupling the pouch (not shown) to the flange 22 of the wafer 20.

The dimensions of the rod 10 and the diameter of the flange 22 are dictated by the diameter of the exteriorized bowel. Thus, several different size kits are typically needed since different patients with different sized exteriorized bowel loops require different sized rods. In many instances, it is deemed prudent to secure the rod with stitches despite the presence of the cross pieces 12, 14. Other commercially available rods of alternative designs must be sutured to the skin to prevent dislodgement.

SUMMARY OF THE INVENTION

It is therefore an object of the invention to provide a loop ostomy device.

It is also an object of the invention to provide a loop ostomy device which is usable with an exteriorized bowel of any caliber and various appliance sizes.

It is still another object of the invention to provide a loop ostomy device which is secure without the need for stitches.

It is yet another object of the invention to provide a loop ostomy device which is easy to use, apply and remove and which affords and allows facile replacement of the ostomy appliance while the device is maintained in situ.

It is still another object of the invention to provide a loop ostomy device which is inexpensive to manufacture.

It is yet another object of the invention to provide a method of using a loop ostomy device.

It is also an object of the invention to provide a method of using a loop ostomy device which is usable with an exteriorized bowel of any caliber and various appliance sizes.

It is still another object of the invention to provide a method of using a loop ostomy device which is secure without the need for stitches.

In accord with these objects which will be discussed in detail below, the loop ostomy device of the present invention includes a flexible rod having coupling members at its ends. The diameter length, and stiffness of the rod are pre-selected such that the rod can be inserted through the mesentery of the bowel, folded upward to lie within the pouch and, optionally, form a loop with both ends of the rod coupled to each other via coupling members. A single size rod according to the invention can be used with bowel of any caliber and with a variety of different sized wafers with different diameter flanges. As a result, a hospital need not stock different If sized rods or loop ostomy appliance kits. In addition, the coupling members obviate the need for any stabilizing stitches. The rod is sufficiently rigid to support the bowel but sufficiently flexible to allow it to bend upwardly so as to maintain it within the confines of the flange of the wafer and the attached ostomy pouch (not shown), and optionally, to allow it to loop and couple one end to the other.

According to the presently preferred embodiment, the rod is made of 0.25 inch diameter plastic (PVC) tubing having a 95 Shore A hardness and is approximately 9–12 inches long. The presently preferred device is provided with an hermaphroditic, generally arrow-head shaped injection molded coupling member attached to each end. The entire device may be injection molded as a single unit.

According to the methods of the invention, the surgeon mobilizes and exteriorizes a loop of bowel either through the incision he used to access the abdominal cavity or through a secondary aperture created in the abdominal wall to accommodate the ostomy. Preferably, a Penrose drain (a soft tubular rubber drain) is placed through the bowel mesentery and used to provide gentle traction on the bowel and as a temporary handle to keep the bowel exteriorized. The surgeon then closes the incisions but maintains an opening just large enough to accommodate the exteriorized bowel. An end of the device according to the invention is then maneuvered through the bowel mesentery to replace the Penrose drain.

If a Penrose drain is not used, and the bowel held temporarily outside the body by some other means, then an aperture is created in the bowel mesentery with a clamp, which is then used to grasp the end of the device of the invention and draw the device through the mesentery. The two ends are then folded up and, optionally, interlocked so that the appliance forms a continuous loop around the bowel. The ostomy can then be matured. Maturation of an ostomy involves opening the bowel and circumferentially suturing the opening of the bowel to the skin defect. A wafer with a flange is then prepared and placed around the looped device and the bowel loop and fixed to the skin. The pouch is then attached to the wafer by joining their respective flanges.

The device is sufficiently flexible to form a loop around the bowel. With the coupling members interlocked or not, the device conveniently bends to fit inside an ostomy pouch. This allows the ostomy pouch to form an uninterrupted seal around the ostomy against the patient's skin. Leakage is thereby avoided. However, the device is sufficiently rigid to prevent the bowel loop from retracting into the abdominal cavity.

The shape of the coupling members allows easy passage through the mesentery for placement of the device, but prevents dislodgement. Interlocking the two coupling members makes dislodgement even more unlikely.

The device is provided to the surgeon as one unit, and does not require assembly. No suturing is required to secure the device to the skin or subcutaneous tissue. The device is less clumsy than the prior art devices and its use speeds the surgical procedure.

To remove the device it is severed at its most narrow portion between the main tube and the coupling members. This can be done without even taking off the ostomy pouch because of the mobility of the device beneath the bowel.

Additional objects and advantages of the invention will become apparent to those skilled in the art upon reference to the detailed description taken in conjunction with the provided figures.

BRIEF DESCRIPTION OF THE DRAWINGS

FIGS. 6A and 6B are top and side elevation views of an ostomy device according to the invention.

DETAILED DESCRIPTION OF THE PREFERRED EMBODIMENTS

Figure 1:
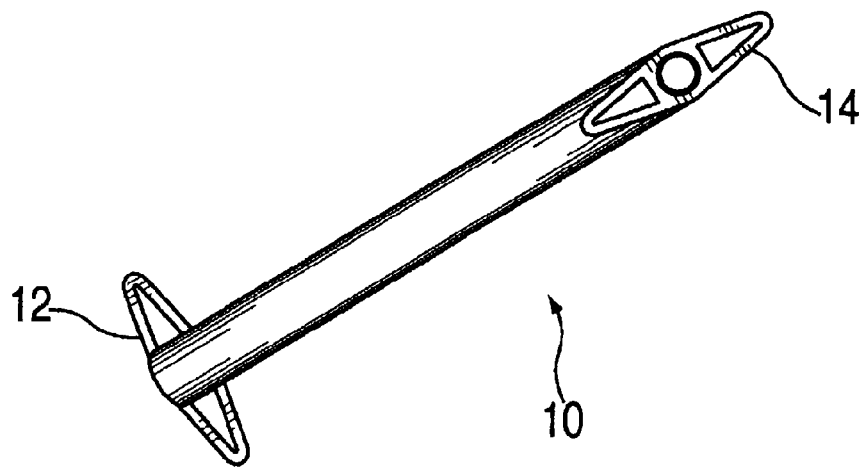
FIG. 1 is side elevation view of a prior art ostomy device.
Figure 2:
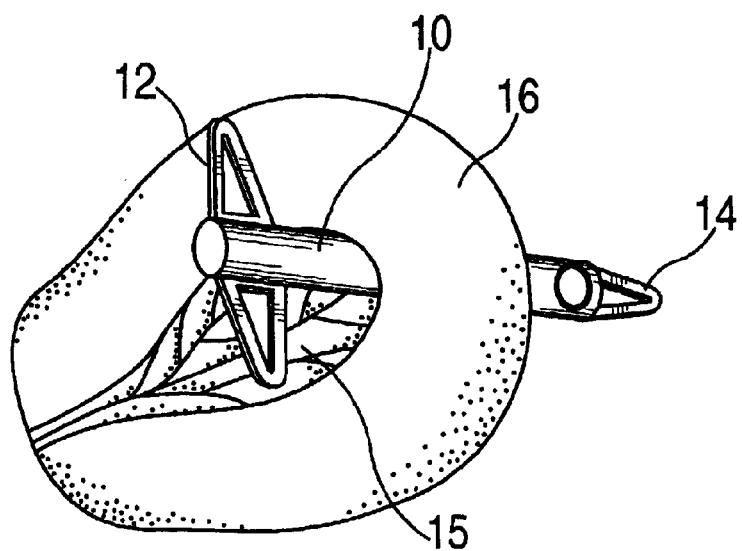
FIGS. 2–5 illustrate how the prior art ostomy device is used.
Figure 3:
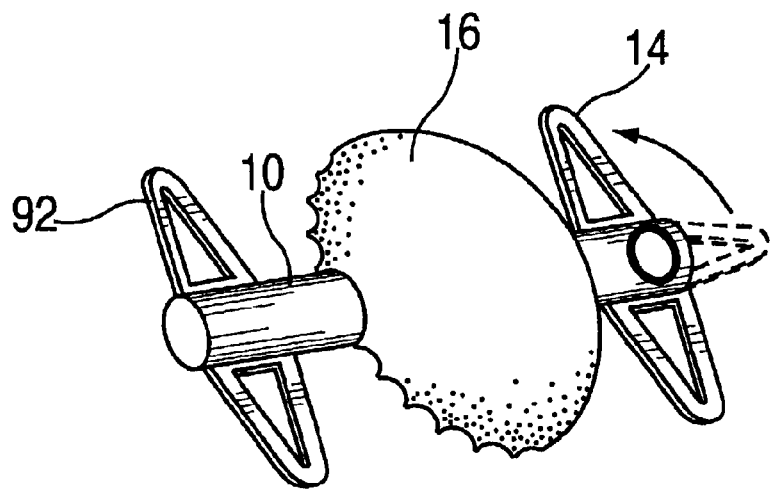
Figure 4:
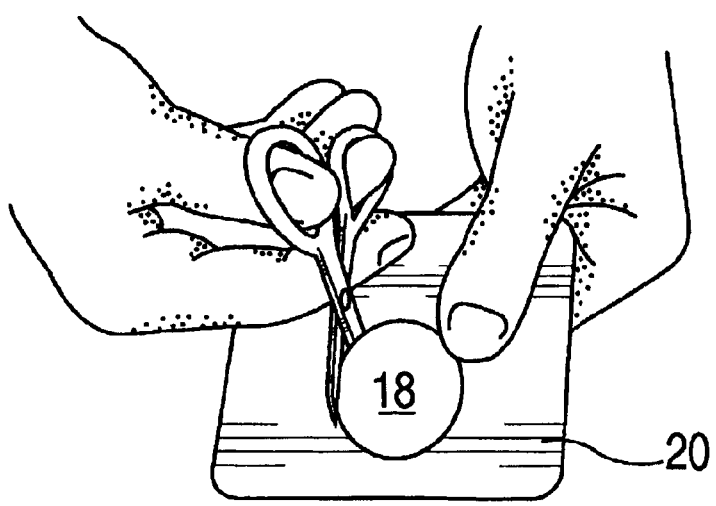
Figure 5:
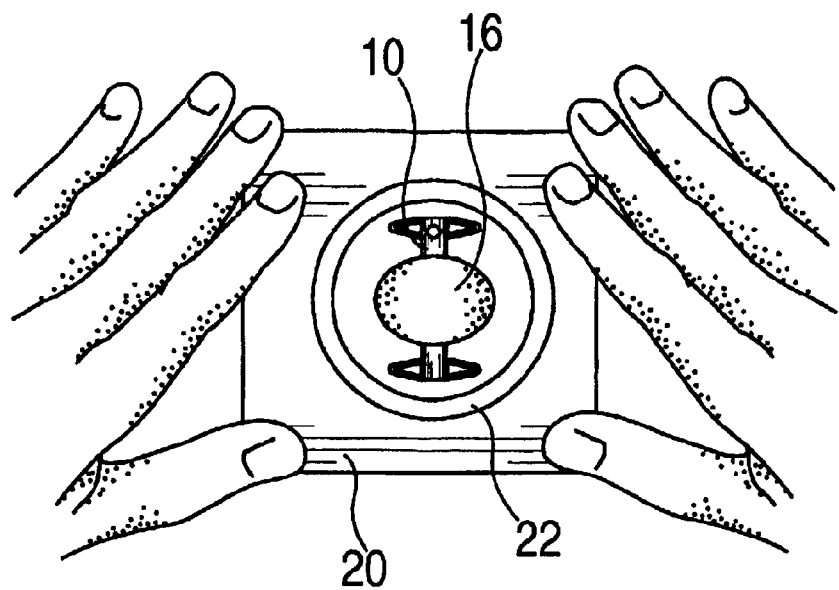

Turning now to FIGS. 6A and 6B, the loop ostomy device 100 of the present invention includes a preferably plastic, flexible cylindrical rod or tube 102 having coupling members 104, 106 at its ends. The diameter and length of the rod 102 are pre-selected such that the rod can be inserted through the mesentery of a bowel, and the ends of the rod are generally folded upward to form a U-shaped or open loop. The rod is designed to optionally enable it to be bent into a closed loop whereby both ends of the rod 102 can be coupled to each other with the coupling members 104, 106. A single size rod 102 according to the invention can be used with bowel of any caliber and a variety of different sized wafers with different diameter flanges. In addition, the coupling members 104, 106 obviate the need for any stabilizing stitches. The rod 102 is sufficiently rigid to support the bowel but sufficiently flexible to allow it to loop and couple one end to the other, as noted above.

According to the presently preferred embodiment, the rod 102 is made of 0.25 inch diameter PVC tube having a 95 Shore A hardness and-is approximately 9–12 inches long. The presently preferred appliance is provided with hermaph- roditic coupling members 104, 106 attached to each end by a relatively narrow plug or cap member 107, 108 which has a cylindrical free end 107a, 108a which fit into the opening 102a of tube 102. Cap members 107, 108 are bonded to rod 102 by adhesive, head sealing and/or any other suitable means. Alternatively, the device may be injection molded as a single unit.

As shown in the figures, each generally arrow-head-shaped coupling member 104, 106 is formed to have a relatively wide base 104a, 106a (e.g. a truncated triangle), a relatively narrow nose 104b, 106b, and a longitudinal slot 104c, 106c. The coupling members are preferably shaped in such a configuration so as to define a narrow insertion end 104b, 106b to facilitate passing the rod through the mesentery of the bowel and a wide wedge-shaped base 104a, 106a which minimizes inadvertent or unintended slippage or withdrawal of the rod from the mesentery. Those skilled in the art will appreciate, however, that the coupling members may be made in different configurations and need not be hermaphroditic.

Figure 7:
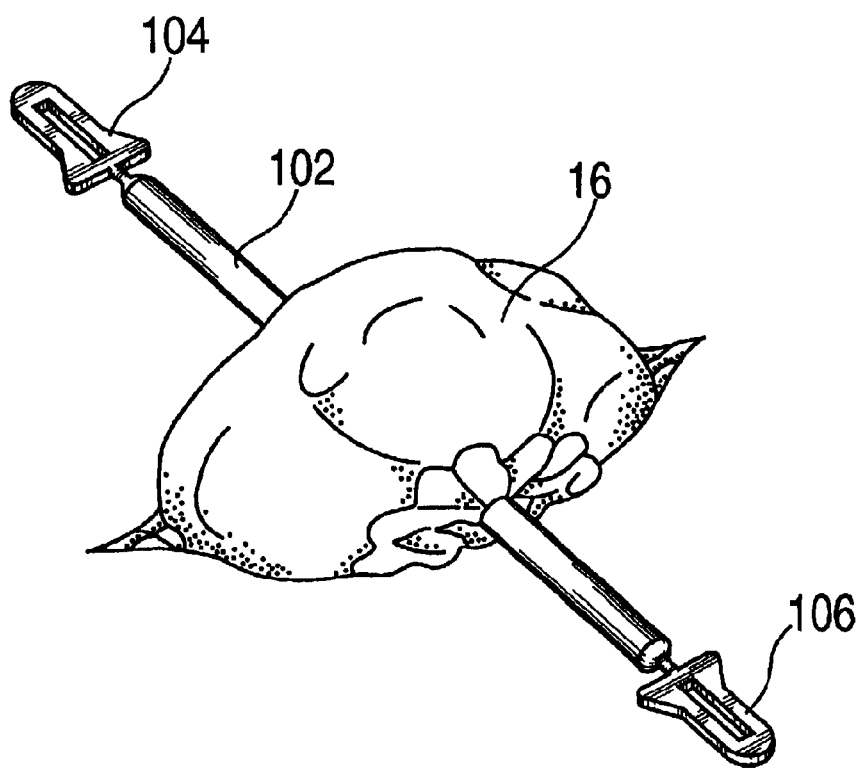
FIGS. 7–9 illustrate how the ostomy device of the invention is used.

According to the methods of the invention, the surgeon mobilizes and exteriorizes a loop of bowel either through the incision he used to access the abdominal cavity or through a secondary aperture created in the abdominal wall to accommodate the ostomy. Preferably, a Penrose drain (a soft tubular rubber drain—not shown) is placed through the bowel mesentery and used to provide gentle traction on the bowel and as a temporary handle to keep the bowel exteriorized. The surgeon then closes the incisions but maintains an opening just large enough to accommodate the exteriorized bowel. An end of the device 100 according to the invention is then maneuvered through the bowel mesentery to replace the Penrose drain. If a Penrose drain is not used, and the bowel held temporarily outside the body by some other means, then an aperture is created in the bowel mesentery with a clamp, which is then used to grasp the end of the device 100 of the invention and draw the device through the mesentery. In either case, the bowel 16 and the rod 102 assume the configuration shown in FIG. 7.

Figure 8:
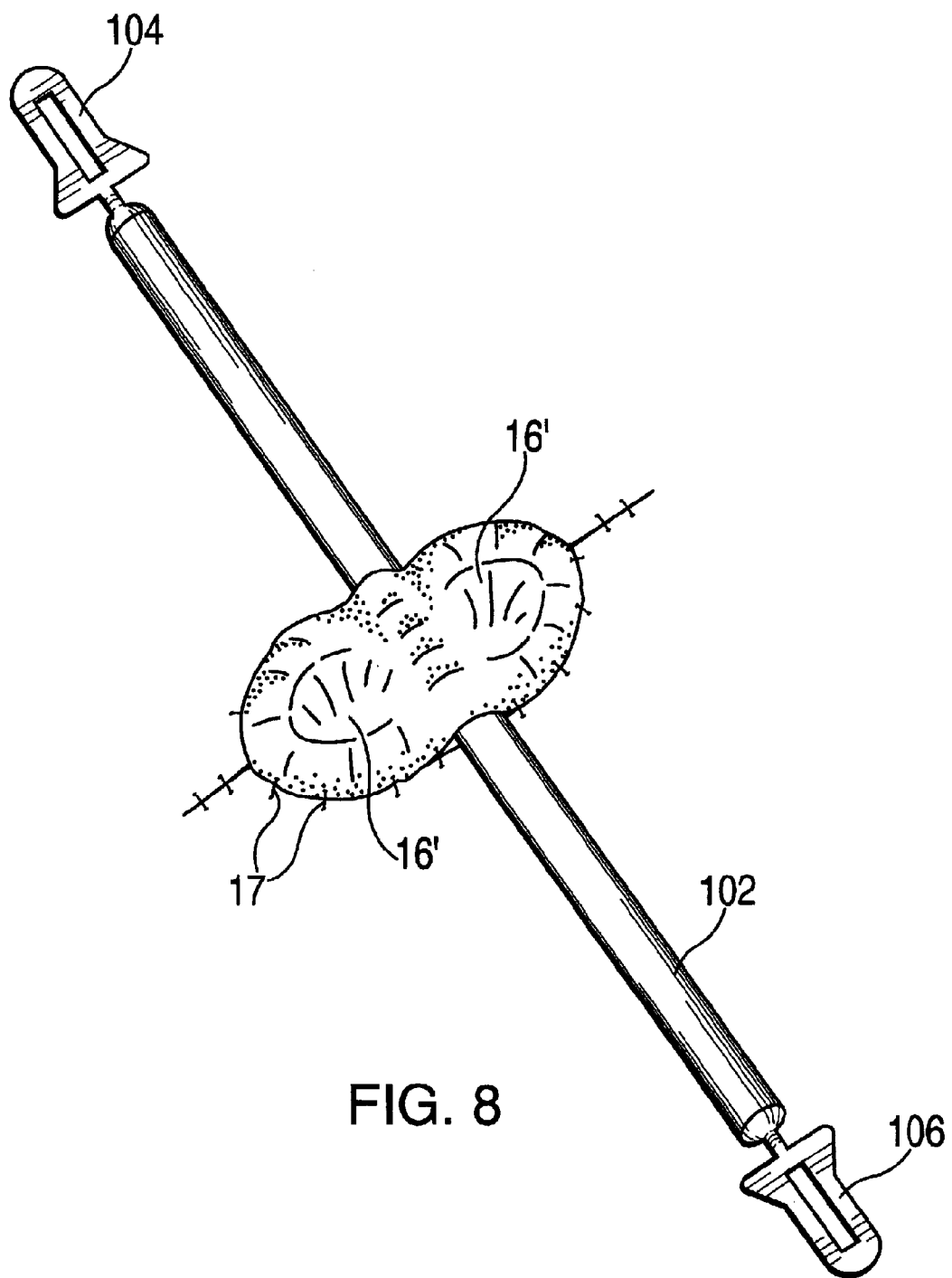

The ostomy can then be matured. Maturation of an ostomy involves opening the bowel and circumferentially suturing the opening of the bowel to the skin defect as shown by sutures 17 in FIG. 8.

Figure 9:
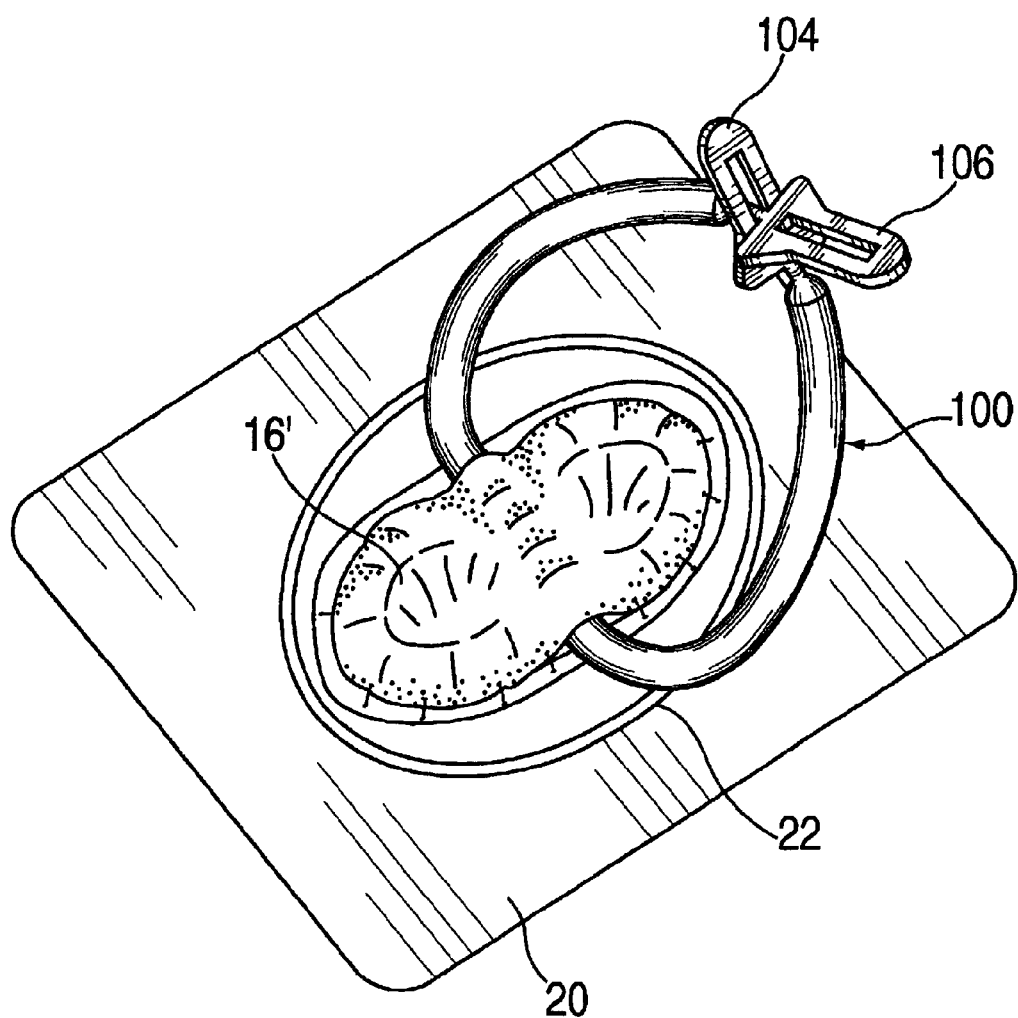

Turning now to FIG. 9, a wafer 20 with coupling flange 22 is then prepared, i.e., a center portion of the wafer 20 is removed by scissors or the like to produce an opening bordered by flange 22 sufficient to accommodate the matured ostomy 16'. The wafer 20 is placed around the device 100 and the matured ostomy 16' and fixed to the skin via its adhesive backing (normally covered by a release strip—not shown).

The two coupling members 104, 106 are then optionally interlocked by inserting one of the coupling members 104, 106 through the slot 104c, 106c of the other and twisting the coupling member passed through the slot so that it is disposed at an angle to the slot, thereby forming a releasable mechanical interlock. As a result, device 100 forms a continuous or closed loop around the bowel 16' as shown in FIG. 9.

At this point, the pouch may be releasably coupled to the wafer flange via its mating flanged open end (not shown).

From the foregoing, it will be appreciated that device 100 is sufficiently flexible to form a loop around the bowel. With the coupling members interlocked or not, the device conveniently bends to fit through an opening cut in the wafer and inside an ostomy pouch. This allows the ostomy appliance to form an uninterrupted seal around the ostomy against the patient's skin. Leakage is thereby avoided. However, the device is sufficiently rigid to prevent the bowel loop from retracting into the abdominal cavity.

The shape of the coupling members allows easy passage through the mesentery for placement of the device, but prevents dislodgement. Interlocking the two coupling members makes dislodgement even more unlikely.

The device is provided to the surgeon as one unit, and does not require assembly. No suturing is required to secure the device to the skin or subcutaneous tissue. The device is less clumsy than the prior art devices and its use speeds the surgical procedure.

To remove the device, it is severed at either neck 107*b* or 108*b*. This can be done without even taking off the ostomy pouch because of the mobility of the device beneath the bowel.

There have been described and illustrated herein several embodiments of a loop ostomy device and methods for its use. Of course, various modifications may be made as will be apparent to those skilled in the art. For example, although the rod is preferably provided with generally arrow-head shaped coupling members, other configurations are possible. Thus, while particular embodiments of the invention have been described, it is not intended that the invention be limited thereto, as it is intended that the invention be as broad in scope as the art will allow and that the specification be read likewise.

What is claimed is:

1. A loop ostomy device comprising:
    a) a flexible rod having a first end and a second end, wherein said flexible rod is rigid enough to support a bowel loop and flexible enough to form a loop whereby said first and second coupling members may interlock;
    b) a first coupling member coupled to said first end; and
    c) a second coupling member coupled to said second end, wherein
        at least one of said coupling members is configured with a relatively narrow nose and a relatively wide base having a width greater than said flexible rod, said relatively narrow nose facilitating passing of the device through the mesentery of the bowel while said relatively wide base provides resistance preventing its unintended removal.

2. A loop ostomy device according to claim 1, wherein at least one of said coupling members has an elongated slot formed therein dimensioned to allow the other coupling member to pass therethrough.

3. A loop ostomy device according to claim 1, wherein said first and second coupling members have a generally arrow-head-shaped configuration.

4. A loop ostomy device according to claim 1, wherein:
    said flexible rod is made of plastic.

5. A loop ostomy appliance according to claim 1, wherein:
    said flexible rod has a Shore A hardness of approximately 95.

6. A loop ostomy device according to claim 1, wherein:
    said flexible rod has a diameter of approximately 0.25 inch.

7. A loop ostomy device according to claim 1, wherein:
    said flexible rod has a length of approximately 9–12 inches.

8. A loop ostomy device according to claim 1, wherein:
    said coupling members are hermaphroditic.

9. A loop ostomy device according to claim 1, wherein:
    at least one of said coupling members is connected to said flexible rod by a relatively narrow member.

10. A loop ostomy device according to claim 11, wherein:
    said relatively narrow member has a diameter of approximately 0.09 to 0.10 inch.

11. A method for performing a loop ostomy, on a patient said method comprising:
    a) mobilizing and exteriorizing a loop of bowel;
    b) passing a flexible ostomy rod through the bowel mesentery;
    c) bending the ends of said rod in a direction generally away from the patient;
    d) placing a wafer having a generally centrally-located opening, and a flange extending peripherally around said opening on said patient around said bowel loop and rod such that said rod and bowel loop are maintained within a perimeter defined by said flange; and
    e) affixing said wafer to the patient's skin.

12. A method according to claim 11, further comprising:
    f) connecting the ends of the rod to form a closed loop.

13. A method according to claim 14, wherein:
    the rod has a coupling member at each end and is substantially continuously flexible along its length between the coupling members and wherein said coupling members are releasably coupled to one another to form said closed loop.

14. A method according to claim 12, wherein at least one of said coupling members has a slot and the other of said coupled members is inserted through said slot to form a closed loop and thereby releasably couple said coupling members together.

15. A method according to claim 11, further comprising:
    f) opening the bowel and circumferentially suturing the opening of the bowel to the skin defect.

\* \* \* \* \*